United States Patent [19]

Powell et al.

[11] Patent Number: 4,539,198
[45] Date of Patent: Sep. 3, 1985

[54] SOLID PHARMACEUTICAL FORMULATIONS FOR SLOW, ZERO ORDER RELEASE VIA CONTROLLED SURFACE EROSION: EXPANDED RANGE

[75] Inventors: David R. Powell; Vithal K. Patel, both of Baudette, Minn.

[73] Assignee: Rowell Laboratories, Inc., Baudette, Minn.

[21] Appl. No.: 511,605

[22] Filed: Jul. 7, 1983

[51] Int. Cl.$^3$ .............. A61K 9/22; A61K 9/32; A61K 9/36; A61K 31/60
[52] U.S. Cl. ................................ 424/19; 424/22; 424/32; 424/35; 514/161; 514/960
[58] Field of Search ............... 424/16, 32, 33, 35, 424/19-22, 230

[56] References Cited

U.S. PATENT DOCUMENTS 4,264,573  4/1981  Powell et al. .................. 424/19
4,361,545  11/1982  Powell et al. .................. 424/19

FOREIGN PATENT DOCUMENTS 2066070A  7/1981  United Kingdom ............. 424/21

OTHER PUBLICATIONS

Porter et al., "The Permeability of Enteric Coatings and the Dissolution Rates of Coated Tablets", Jun. 5, 1981, pp. 5-8.
Remington's *Pharmaceutical Sciences*, 1970, pp. 1689-1691.
Porter, "Tablet Coating," Jun. 1981, pp. 44, 46, 48, 50, 51, 86, 90, 92, 94.
Luce, "Cellulose Acetate Phthalate: A Versatile Enteric Coating", Jun. 1977.
Rasmussen, "5-Aminosalicylic Acid in a Slow-Release Preparation: Bioavailability, Plasma Level, and Excretion in Humans," 1982, pp. 1062-1070.

*Primary Examiner*—Shep K. Rose
*Attorney, Agent, or Firm*—Millen & White

[57] ABSTRACT

A new class of solid pharmaceutical formulations enables the attainment of slow, zero order in vivo release of a wide range of pharmaceutically active ingredients upon oral administration. A broad range of release rates can be preselected by suitable adjustments of tablet properties. The formulations are based upon control of active ingredient release from the surface of the tablet via a controlled surface erosion mechanism. These compositions comprise:

(a) an effective amount in the range of 10-90 wt. % of a pharmacologically active compound having a water solubility (20° C.) of 1/5-1/1000 (w/w);
(b) 1-40 wt. % of a compound which is pharmaceutically acceptable in oral compositions and has a water solubility (20° C.) of 1/1-1/40 (w/w);
(c) 2-20 wt. % of a compound which is pharmaceutically acceptable in oral compositions and has a water solubility (20° C.) of 1/1-1/10 (w/w);
(d) an amount in the range of 0.05-1.0 wt. % of a disintegrating agent for pharmaceutical compositions, at which amount the compound is ineffective as a disintegrating agent;
(e) 0.1-2.0 wt. % of a surfactant which is pharmaceutically acceptable in oral compositions; and, as necessary for tablet manufacturing purposes;
(f) 1-20 wt. % of a binder which is pharmaceutically acceptable in oral compositions; or
(g) 0.5-5.0 wt. % of a die wall lubricant which is pharmaceutically acceptable in oral compositions.

12 Claims, No Drawings

SOLID PHARMACEUTICAL FORMULATIONS FOR SLOW, ZERO ORDER RELEASE VIA CONTROLLED SURFACE EROSION: EXPANDED RANGE

CROSS REFERENCE TO RELATED APPLICATIONS

This application is related to U.S. Pat. Nos. 4,361,545 and 4,264,573, the former being a continuation-in-part of the latter. The disclosures of these patents are incorporated by reference herein in their entireties.

BACKGROUND OF THE INVENTION

The present invention relates to solid pharmaceutical formulations whereby, upon oral administration, the active ingredients are released with a selectable, usually slow, zero order rate.

Various techniques are known for formulating active ingredients to selectively control the resultant release rate of the drug, e.g., via sustained release, slow release, fast release, etc.

It is important for any pharmaceutical formulation technique to provide the capability of preselecting a desired release rate which can be tailored to the unique characteristics of each drug. For example, many formulations exist which permit selection of very slow release rates, i.e., sustained release formulations. (See, e.g., U.S. Pat. No. 3,641,236 based upon glycerol fatty acid esters and U.S. Pat. No. 3,950,508 based upon alkyl celluloses and inert powders such as talc, which, in combination with other ingredients, produce a gradual disaggregation of the sustained release tablet.) These can often cause toxicity and other side effects due to an inordinately long presence of the drug in the body. Thus, methods of preselecting somewhat faster release rates, i.e., slow release rates—midway between fast and sustained rates—are needed.

Moreover, as Zaffaroni has suggested (Therapeutic Implications of Controlled Drug Delivery, Future Trends in Therapeutics, Ed. F. C. McMahon, Mount Kisco, N.Y., Futura Publishing, 1978, pp. 143–160), an ideal drug delivery system would allow a constant amount of drug to be absorbed per unit of time (zero-order kinetics). Thus, serum concentrations would not fluctuate under steady-state conditions. Weinberger et. al., The New England Journal of Medicine, Vol. 299, No. 16, Oct. 19, 1978, pp. 852-857, have stated: "Modern technology related to controlled oral delivery systems should be applied to theophylline in an attempt to approximate zero-order absorption so that the continuous stabilizing effect of this drug on the airways can be maintained in the most effective, convenient and risk-free manner." Similar sentiments have been echoed by many pharmaceutical researchers in recognizing the preference for and importance of zero order release rates for many drugs. See, e.g., U.S. Pat. No. 3,965,255. Nevertheless, zero order release has rarely been achieved; there is no available technique by which a selected drug can be systematically formulated to provide zero order release kinetics in vitro or in vivo.

Furthermore, many formulations result in a bioavailability curve having a high concentration peak at the beginning of release with a subsequent tailing off at longer times. Such concentration peaks are generally undesirable since they can lead to toxicity and/or other adverse side effects. Additionally, they significantly limit the freedom to increase the unit dosage of administration. Such an increased dosage would correspondingly increase the peak concentration. Under such circumstances, it is not possible to decrease the frequency of administration by increasing the unit dosage. This is a significant disadvantage in view of the well established correlation between the likelihood that a patient will fail to take doses of his medication and the required frequency of administration. Zero order release would attenuate this adverse effect by regulating the amount of active ingredient released in vivo per unit of time.

As can be seen, in most instances, it is desirable to achieve a relatively slow, zero order release rate of medication. This precise rate should be easily selectable so that the resultant in vivo absorption is desirably controlled and the bioavailability of the drug is maximized.

SUMMARY OF THE INVENTION

Accordingly, it is an object of this invention to provide slow release pharmaceutical formulations the amounts of whose ingredients can be readily adjusted to provide in vivo, zero order release for the active ingredient(s).

It is another object of this invention to provide such pharmaceutical formulations by which the release rate and release curve shape can be controlled in order to maximize in vivo bioavailability of the active ingredient and/or minimize side effects.

It is still another object of this invention to provide such formulations which can be reproducibly manufactured by conventional pharmaceutical methodology.

It is yet another object of this invention to provide such formulations which are based on the principle of controlled surface erosion and represent a significant modification and expansion of the formulations of U.S. Pat. No. 4,361,545.

It is a further object of this invention to provide such formulations comprising, as active ingredient, 5-aminosalicylic acid (5-ASA).

Upon further study of the specification and appended claims, further objects and advantages of this invention will become apparent to those skilled in the art.

These objects have been attained by providing a solid, orally administrable pharmaceutical composition from which the active ingredient has a slow, zero order in vivo release rate when administered orally, comprising:

(a) an effective amount in the range of 10–90 wt. % of a pharmacologically active compound having a water solubility (20° C.) of 1/5–1/1000 (w/w) which, notably, includes the new range of less than 1/500 to 1/1000;

(b) 1–40 wt. % of a compound which is pharmaceutically acceptable in oral compositions and has a water solubility (20° C.) of 1/1–1/40 (w/w);

(c) 2–20 wt. % of a compound which is pharmaceutically acceptable in oral compositions and has a water solubility (20° C.) of 1/1–1/10 (w/w);

(d) an amount in the range of 0.05–1.0 wt. % of a disintegrating agent for pharmaceutical compositions, at which amount the compound is ineffective as a disintegrating agent;

(e) 0.1–2.0 wt. % of a surfactant which is pharmaceutically acceptable in oral compositions; and, if necessary for tablet manufacturing purposes, (f) 1–20 wt. % of a binder which is pharmaceutically acceptable in oral compositions; or (g) 0.5–5.0 wt. % of a die wall lubricant which is pharmaceutically acceptable in oral compositions, the pharmacologically active compound thus having a slow, zero order in vivo release rate when administered orally.

In another aspect, this invention provides a method of orally administering an active ingredient to a patient in need of treatment therewith, such that the drug is released in vivo with a slow, zero order release rate, comprising orally administering a pharmaceutical composition of this invention to such a patient.

In still another aspect, this invention provides a combination of such a composition and an enteric coating whereby the onset of the release of the drug is delayed until the composition reaches a desired point in the gastrointestinal tract, e.g., when the active agent is 5-ASA.

DETAILED DISCUSSION

In one aspect, this invention provides a significant expansion of the applicability of the controlled surface erosion principles of U.S. Pat. No. 4,361,545 in formulating pharmacologically active compounds for zero order release. It has now been found that drugs of a solubility in the low range of less than 1/500 to 1/1000 can be formulated according to the details thoroughly described in U.S. Pat. No. 4,361,545. This is a surprising and unexpected result since, heretofore, it was thought that this formulation technique was inapplicable to drugs having a solubility less than 1/500 (w/w).

Since all of the disclosures of U.S. Pat. No. 4,361,545 have been incorporated by reference herein, and since, unless indicated otherwise herein, all are fully applicable to this invention, the following will summarize only a portion of these details, for purposes of clarity. Examples relating to this new range are also included.

Any drug of appropriate solubility can be formulated in accordance with this invention. Especially suitable are those for which there exists a specific reason for achieving zero order release and/or other release curve shape effects, such as minimizing peak serum levels. For example, such drugs include antibiotics, cardiovascular agents, analgesics, antipyretics, antiinfectives, antacids, gastrointestinal medications, steroids, CNS stimulants, psychopharmacologic drugs, antineoplastic and immunosuppressive drugs, antihistaminics, vitamins, essential minerals, sympathomimetic and parasympathomimetic drugs, antitussives, diuretics, sedatives, hypnotics, antiepileptics, decongestants, antiasthmatics, etc. (Lithium formulations are the subject of the claims of U.S. Pat. No. 4,264,573 mentioned above, and are excluded from the claims of this application.)

In general, the amount of the active ingredient will be 10-90% by weight of the tablet, or higher, e.g., 30-90%, typically 50-90%. The drug should have a solubility in water (20° C.) of about 1 weight part in 5 weight parts to 1 weight part in 1000 weight parts, e.g., 1/5-1/500 or <1/500 to 1/1000, e.g., 1/10-1/500 w/w or for the new regime of this invention, <1/500 to about 1/800, 1/560-1/1000, or about 1/800 w/w, etc. For many typical drugs, the solubility is 1/50-1/300 w/w. In general, the half-life of the drug will not be a factor since the formulation of this invention does not produce sustained release but rather slow, controlled release.

In addition to its role as a medicament, the active ingredient also affects the precise release rate which is obtained, primarily by contributing towards penetration control and cohesion because of its solubility.

Ingredient (b) is termed the "surface controller" and functions primarily as a surface uniformity control agent during dissolution and erosion. The selection of a particular agent is not especially critical as long as it is a pharmaceutically acceptable excipient which is of the proper water solubility and compatible with oral tablet manufacturing. Preferably, the agent should have a water solubility (20° C.) of about 1 weight part in 1 weight part to 1 weight part in 40 weight parts; e.g., 1/1-1/20 w/w. Typically the solubility is ½ to 1/30 w/w. It is usually employed in amounts of 1-40% by weight of the final tablet, typically 3-30 wt. %.

Suitable pharmaceutical excipients useful as surface controllers include the generally preferred inorganic compounds such as the chloride, sulfate and phosphate salts of potassium, sodium and magnesium as well as the calcium citrate, phosphate, lactate, gluconate and succinate salts. Suitable organic compounds for use as the surface uniformity control agent include pharmaceutically acceptable mono-saccharides and di-saccharides and the corresponding polyhydroxy alcohols, for example, glucose, fructose, lactose, dextrose, xylose, galactose, sucrose, maltose, sorbitol, mannitol and xylitol. Other candidates include natural amino acids and organic carboxylic or sulfonic acids.

Ingredient (c) is termed the "erosion controller" and serves as the primary erosion rate controlling agent. Consequently, this ingredient generally has a high water solubility, e.g., about 1 weight part in 1 weight part to 1 weight part in 10 weight parts, e.g., 1/1-1/5 w/w, typically 1/1 to 1/5 w/w. Suitable such agents also include pharmaceutically acceptable mono- and disaccharides and the corresponding polyhydroxy, i.e., polyhydric alcohols, natural amino acids, and organic carboxylic or sulfonic acids, all of which is general should be suitable for dry mixing with the active granulations or powders. For example, such agents include sorbitol, mannitol, xylitol, lactose, glucose, xylose, galactose, maltose, sucrose, dextrose, fructose, etc. The amount of this ingredient is selected, inter alia, in accordance with the desired rate of dissolution erosion and generally is in the range of 2-20% based on the weight of the final tablet, e.g., 0.1-50, typically 3-10 wt. %, e.g., 5-10 wt. %.

Ingredient (d) of the inventive composition is termed the "surface activator". Per se, these are fully conventional disintegration agents employed in oral pharmaceutical tablets. However, they are employed in amounts at which they are ineffectual as disintegrating agents. Of course, since the formulations of this invention are to provide slow release, effective amounts of these ingredients would be incompatible. In fact, effective amounts would destroy the controlled erosion phenomenon.

Instead of the conventional disintegrating effect, in the heretofore never used low amounts, these disintegrating agents serve primarily to stabilize the controlled erosion phenomenon over long term storage of the solid compositions. To some degree, they also affect the finally achieved erosion rate, and correspondingly, the release rate. This is probably accomplished through penetration control effects. In other words, without these low amounts of the surface activator, the zero order nature of the release rate of the solid compositions could be accomplished but could not be stably maintained over the long storage periods required in the pharmaceutical field, e.g., 2-5 years, typically 3 years.

As can be seen, this is a necessary ingredient in the commercial pharmaceutical tablets of this invention.

Such conventional disintegrating agents include starch and starch derivatives, wood and cotton cellulose derivatives of the microcrystalline or crosslinked types or other polymeric materials etc. which are conventional disintegrants; see, e.g., Shangraw, et. al., Pharmaceutical Technology, October, 1980, pp. 49–57 whose disclosure is incorporated by reference herein. These surface activators are employed in low, disintegrant ineffective but surface activator effective concentrations of 0.05–1.0 wt. %, typically 0.05–0.5 wt. %.

Ingredient (e) is a surface active agent which is also pharmaceutically acceptable and fully conventional for use in oral tablets. This ingredient provides wettability for any hydrophobic components such as the stearates and also affects medium penetration and surface erosion to some extent. Suitable such conventional surfactants include sodium lauryl sulfate, magnesium lauryl sulfate, dioctyl sodium sulfosuccinate, triethanolamine, polyoxyethylene sorbitan, poloxalkol derivatives and quaternary ammonium salts. In general, the surfactants have hydrophile-lipophile balance ratios (HLB) of above 12. Surface active agents are generally included in the composition in amounts of 0.1–2% by weight of the final tablet, typically 0.15–1.0 wt. %.

Under ideal circumstances, ingredients (a)–(e) would be sufficient to achieve all purposes of this invention including zero order release rates for the active ingredient in accordance with the controlled erosion phenomenon. Such five component formulations, however, will be rare since almost all active ingredients require additional excipients to satisfy the demands of the tablet manufacturing steps. Such tableting ingredients include the familiar binders and dye wall lubricants, i.e., ingredients (f) and (g) mentioned above.

Ingredient (f) of the pharmaceutical composition of this invention is a fully conventional pharmaceutically acceptable binder for oral tablets. These are normally employed to aid in the formation of granules during the granulation step(s), to modify the compression characteristics during the compression steps, or to aid during other conventional tablet forming processes. As mentioned, the compositions of this invention achieve slow release at zero order using only the relatively soluble ingredients discussed above. Binders, e.g., gums, waxes, relatively insoluble polymers, etc., previously needed to achieve such slow release rates in conventional sustained release compositions and many other slow release compositions, are obviated. These ingredients are employed only where desirable, or necessary for tableting purposes, per se.

Suitable such fully conventional pharmaceutical binders include povidone (polyvinylpyrrolidone), polyvinylalcohol, polyethyleneglycol, sucrose, lactose, gelatin, starch paste, acacia, tragacanth, etc.

In general, when present, the binders are included in the inventive pharmaceutical composition in amounts of 1–20% by weight, of the final tablet, typically 1–5 wt. %. When binders are absent, the composition of this invention will be inherently compressable and/or granulatable, e.g., by the slugging technique or by the addition of a subsequently evaporatable, activating solvent such as water, alcohol, acetone, etc. In addition to the primary binding effect of this ingredient, wettability control and penetration control will sometimes be affected to some degree by its inclusion, depending, of course, on the specific characteristics of the particular binder employed.

Ingredient (g) is a fully conventional, pharmaceutically acceptable die wall lubricant for inclusion in oral tablets. This ingredient is required in order to facilitate the ejection of the tablet from the die after the compression step by lubrication of the tableting tool. Suitable such conventional die wall lubricants include the stearate salts such as calcium, magnesium, and zinc, as well as stearic acid, mineral oil, vegetable oil derivatives, polyethylene glycols, talc, etc. In general, 0.5–5% by weight of the final tablet of this ingredient is included, i.e., amounts in which these ingredients function as die wall lubricants, typically 1–4 wt. %.

Ingredients (e) and (g) may also be added to the composition in conventionally combined form. Such combinations are commercially available and are provided as a homogeneous mixture of the two ingredients prepared by spray drying or other techniques. Such commercially available combined lubricants and surface active systems include Stear-o-wet C and Stear-o-wet M.

Very often, an active ingredient is dosed in high concentrations. Typical such high dosage drugs include lithium, theophylline, quinidine sulfate, etc. Such drugs are dispensed in unit dosages from 50–500 mg, for example. For other high dosage drugs, unit dosages are as high as 1000 or 1500 mg. Such dosages are quite readily compatible with the pharmaceutical composition of this invention as defined above. However, it is often desired to formulate drugs in dosage ranges of less than 50 mg, e.g., 1–<50 mg per tablet yet still retain conventionally sized tablets. In such situations, ingredient (h) can be incorporated into the tablet replacing a corresponding amount of the active ingredient per se. In this way, slow release base formulations for the more potent type of drugs can be prepared at low dosages.

Since excipients (h) are used to replace active ingredient (a), they should have the same solubility properties, e.g., water solubilities (20° C.) of about 1 weight part in 5 weight parts to 1 weight part in 1000 weight parts, e.g., 1/5–1/500 or <1/500 to 1/1000, e.g., 1/10–1/500 w/w or for the new regime of this invention, <1/500 to about 1/800, 1/560–1/1000, or about 1/800 w/w, etc. For many typical drugs, the solubility is 1/50–1/300 w/w. The amount of this innocuous bulking excipient, i.e., inert filler, is to be chosen depending upon the desired dosage of the active ingredient as well as the other factors discussed above with respect to the active ingredient per se. Generally, the amount of ingredient (h) is 1–80% by weight of the finally produced tablet, depending on the desired tablet size.

Such innocuous bulking excipients (fillers) are fully conventional and include the pharmaceutically acceptable excipients for oral tablets such as inorganic salts, both mineral and mineral organic, carbohydrates, proteins, emulsifiable fats and the like. Specific examples include calcium salts, such as the lactate, gluconate, glycerylphosphate, citrate, phosphate monobasic and dibasic, succinate, sulfate and tartrate, as well as the same salts of aluminum and magnesium. Typical such carbohydrates include the conventional mono- and disaccharides as well as the corresponding polyhydric alcohols.

Manufacture of the formulations is in accordance with the details given in the mentioned U.S. Pat. Nos. 4,361,545 and 4,264,573. As mentioned therein, coatings can be used on the formulations of this invention to tailor the onset of drug release for a given purpose, e.g., to delay it until the formulation reaches a desired location of the gastrointestinal tract, e.g., enteric coatings which enable bypassing of the stomach and initiation of release in the small intestine. The manufacture, design and compositions of such coatings are fully conventional, e.g., as disclosed in Porter et al, "The Permeability of Enteric Coatings and the Dissolution Rates of Coated Tablets", J. Pharm. Pharmacol. 1982: 34:5–8; Remington's Pharmaceutical Sciences, Ed. Osol et al, e.g., 1689–1691, 14th Ed., Mack Publishing Co. (1970); Porter, "Tablet Coating", Drug & Cosmetic Industry, June 1981, 44–51, 86–94; Luce, "Cellulose Acetate Phthalate: A Versatile Enteric Coating", Pharmaceutical Technology, June 1977; as well as, data sheets provided with many commercial products such as, Eudragit-L, Eudragit-L (Aqueous Dispersion), Eudragit-S, etc. (all by Rohm and Haas, Germany); PVAP, OPADRY, etc. (all by Colorcon, Inc., West Point, Pa.), etc., all of whose disclosures are incorporated by reference herein. As mentioned, these coatings are not expected to achieve the desired release rate per se—controlled surface erosion accomplishes that. They merely serve as time delays for onset of the release mechanism of this invention.

Drugs in the new solubility range defined in this invention include 5-aminosalicylic acid (5-ASA) which is useful, e.g., to treat ulcerative colitis and Crohn's disease. (See, e.g., Rasmussen et al, Gastroentology 1982:83: 1062–70, whose disclosure is incorporated by reference herein). It is particularly desirable to employ an enteric coating in conjunction with 5-ASA to delay the onset of release of the drug to the small intestine and/or large intestine.* Other drugs in the new solubility range include oxypertine, allobarbitone, allylbarbituric acid, 4-aminosalicyclic acid, amisometradine, carbimazole, cyclobarbitone, salicylic acid, saliclamide, carphenazine maleate, cocaine, dextrothyroxine sodium, metharbital, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

*5-ASA must be delivered to the site of mucosal inflammation to be effective.

EXAMPLE 1

5-ASA Tablets

| Composition | % W/W Typical |
|---|---|
| 5-Aminosalicyclic Acid (5-ASA) | 73.3 |
| Sodium Chloride | 11.7 |
| Povidone** | 4.4 |
| Alcohol SDA-3A, q.s. | — |
| Lactose | 8.8 |
| Calcium Stearate/Sodium Lauryl Sulfate* | 1.76 |
| Sodium Starch Glycolate | 0.29 |

*as defined in Example 2;
**polyvinylpyrrolidone

The sodium chloride is milled through a Whistler mill using a small slotted screen. The 5-ASA is combined with the sodium chloride and mixed for 5 minutes in a ribbon blender. The powder blend is milled through a Fitz mill at high speed (1B band) and returned to the ribbon blender. Povidone/alcohol solution is added to the powder blend while the mixer is running to form a wet mass. The wet mass is passed through a Fitz mill (½ inch, perforated band) with hammers forward at high speed. The wet granulation is trayed and dried for 16 hours at 55° C. The dried mixture is sized through a Fitz mill (2A band) with knives forward at medium speed. The resultant blend is placed in a ribbon blender. Lactose, calcium stearate/sodium lauryl sulfate and sodium starch glycolate is passed through a 40 mesh screen. The screened powders are added to the ribbon blender and mixed for 5 minutes. On a conventional tablet press, the finished granulation is compressed into 3/8" tablets using standard concave tooling. The tablets meet the target weight requirements, are about 0.175 in. thick, have a hardness of 8–15 kilopounds and a friability of NMT 0.4%.

ENTERIC COATING 100 kg of compressed tablets is placed into an Accela-Cota pan and warmed to about 40° C. exhaust temperature. 5 kg of Opadry Enteric (Colorcon, Inc.) is dispersed in an alcohol (SDA-3A)-water mixture (composition of alcohol/water is 25.5 kg and 2.8 kg respectively). This solution is spray coated on tablets using an air-atomization system as follows: 2 spray guns at 35 psi each set to deliver about 60 g/minute, maintaining an exhaust temperature of 35'–45° C. The coated tablets are dried in the Accela-Cota pan for 1 hour at 35°–45° C. The tablets are polished in the pan using 1 gram of powdered Carnauba Wax.

EXAMPLE A PRELIMINARY TESTING

Pilot Batch Formulation and Optimization:
Batch Size: 5000 tablets
Base Granulation:

| | Per Tablet (mg) | % w/w* |
|---|---|---|
| 5-Aminosalicylic Acid | 250 | 72.00 |
| Sodium Chloride | 40 | 11.50 |
| +Plasdone USA | 20 | 5.80 |
| Alcohol SDA-3A (granulating solvent, removed by drying) | — | |

Manufacturing: Wet milling and dry milling of granulation using Homoloid mill.
+: polyvinylpyrrolidone by GAF
*: of final tablet composition

SIZED GRANULATION

Flow: Very good
Tapped Bulk Density: 0.5 gram/ml
Chromatographic Purity Test:
Objective: To detect any interaction between 5-Aminosalicylic Acid and Alcohol SDA-3A (methyl or ethyl ester of 5-ASA).
Rf
5-ASA 0.26
No other foreign spot on the TLC plate.

EXAMPLE 2

Using the base granulation of 5-ASA from Example A and the procedure of Example 1, controlled surface erosion ingredients were added. The formulations are shown below.

| Composition | Function Class | Ingredient weight (mg) 1 | 2 | 3 | % w/w |
|---|---|---|---|---|---|
| 5-Aminosalicylic Acid | a | 250 | 250 | 250 | 72.20 |
| Sodium Chloride | b | 40 | 40 | 40 | 11.50 |
| Plasdone USP | f | 20 | 20 | 20 | 5.80 |
| *Stear-o-wet-C | e/g | 6 | 6 | 6 | 1.70 |
| Sodium Starch glycolate | d | 0.5 | 0.5 | 0.5 | 0.14 |
| Lactose Po. | c | 40 | — | — | 11.50 |
| Mannitol | c | — | 40 | — | 11.50 |
| Sorbitol | c | — | — | 40 | 11.50 |
| Theor. Tablet Weight | | 346.5 | 346.5 | 346.5 | |

*6 mg of Stear-o-wet-C consists of 0.36 mg of sodium lauryl sulfate and 5.64 mg of calcium stearate.
Batch Size: 500 Tablets
Compressed on 'E' machine using ⅜" standard concave tooling, upper and lower plain.

Tablet Formulation Evaluation:

| Test | 1 | 2 | 3 |
|---|---|---|---|
| Compressibility | Excellent | Excellent | Excellent |
| Flow | Very good | Very good | Very good |
| Avg. Tablet Wt. | 348 mg | 342 mg | 344 mg |
| Thickness | 0.177" | 0.177" | 0.178" |
| Hardness | 14 KP | 12 KP | 11 KP |
| Friability | 0.09% | 0.12% | 0.14% |

DISSOLUTION DATA

Dissolution Procedure:
Dissolution Apparatus: USP Method II, (Paddle)
Paddle Rotation Speed: 100 rpm
Dissolution Medium: 900 ml, pH 7.0, phosphate buffer in deaerated water RODI.

| Time, Minutes | *Cumulative % Dissolved of Label Claim 1 | 2 | 3 |
|---|---|---|---|
| 15 | 8.6 | 8.2 | 9.1 |
| 30 | 16.7 | 15.7 | 17.3 |
| 60 | 34.1 | 33.7 | 34.3 |
| 120 | 59.8 | 58.4 | 58.3 |
| 180 | 80.8 | 84.2 | 86.6 |
| Statistical Analysis for fit to zero order release | | | |
| $T_{50\%}$, Minutes | 103.8 | 102.8 | 100.2 |
| Dissolution Rate mg/min. | 1.0945 | 1.1436 | 1.154 |
| Correlation Coefficient (R) | 0.9998 | 0.9992 | 1.004 |
| | | excellent linearity | |

*Avg. of 6 tablets, samples were pooled.

EXAMPLE 3

The formulation used in Example 2 was optimized as follows using the same procedure:

| Ingredient | Function Class | Per Tablet (mg) | % w/w |
|---|---|---|---|
| 5-Aminosalicylic Acid | a | 250 | 72.15 |
| Sodium chloride | b | 40 | 11.54 |
| Plasdone | f | 20 | 5.77 |
| Lactose powder | c | 30 | 8.65 |
| Stear-o-wet C | e/g | 6 | 1.73 |
| Sodium starch glycolate | d | 0.5 | 0.14 |
| Theor. Tablet Weight | | 346.5 | |

Batch Size: 4000 Tablets

COMPRESSION

Using rotary tablet press and ⅜" standard concave tooling, upper and lower plain, excellent compressibility.

TABLETS

Hardness: 13.2 KP
Friability: 0.08%
Wt. Variation: Passes (±1% of avg. wt.)
Average Tablet Wt. = 347.6 mg

DISSOLUTION DATA

5-ASA SR Tablet 250 mg
Dissolution Profile:
Dissolution Procedure: As in Example 2.

| Tablet Number | Cumulative % Dissolved of Label Claim | | | | |
|---|---|---|---|---|---|
| | 15 min. | 30 min. | 60 min. | 120 min. | 180 min. |
| 1 | 9.4 | 16.0 | 36.2 | 78.5 | 105.8 |
| 2 | 7.9 | 16.0 | 30.3 | 62.6 | 99.1 |
| 3 | 8.0 | 16.7 | 31.2 | 69.4 | 101.9 |
| 4 | 8.9 | 17.2 | 31.40 | 68.6 | 104.0 |
| 5 | 8.6 | 17.2 | 33.30 | 71.90 | 102.8 |
| 6 | 9.2 | 17.4 | 31.40 | 62.70 | 100.8 |
| Avg. | 8.66 | 16.75 | 32.3 | 68.95 | 102.4 |
| % RSD | 7.10 | 3.73 | 6.65 | 8.69 | 2.3 |

STATISTICAL ANALYSIS FOR FIT TO ZERO-ORDER RELEASE $T_{50\%} = 86.3$ minutes
Dissolution Rate: 1.43 mg/minute
Correlation Coefficient (R) = 0.9998 (excellent linearity)

EXAMPLE 4

200 tablets were prepared in a continuation of the work performed in Examples 2 and 3 using the same procedures.

| Ingredient | Function Class | Per Tablet (mg) | % w/w |
|---|---|---|---|
| 5-Aminosalicylic Acid | a | 250 | 73.31 |
| Sodium chloride | b | 40 | 11.73 |
| Plasdone | f | 15 | 4.40 |
| Lactose Po. (200 mesh) | c | 30 | 8.80 |
| Stear-o-wet C | e/g | 6 | 1.76 |
| Sodium starch glycolate | d | 0 | 0.0 |
| Alcohol SDA-3A as a granulating solvent | | | |
| Target weight = | | 341 | |

FINISHED GRANULATION

Flow: Very good
Compressibility: Very good
Tablets (Uncoated): Compressed on rotary tablet press using ⅜" standard concave tooling both upper and lower plain.
Average Tablet Wt.: 345 mg Hardness: 10 KP (8–11 KP)
Thickness: 0.176"
Friability: 0.10%
Dissolution Data:
Dissolution Test Procedure: USP dissolution apparatus II (paddle method), 100 rpm, pH 7.0, phosphate buffer in deaerated RODI water, 900 ml.

| Tablet Number | Cumulative % Dissolved of Label Claim Time, Minutes | | | | | |
|---|---|---|---|---|---|---|
| | 15 | 30 | 60 | 120 | 180 | 240 |
| 1 | 6.6 | 12.1 | 23.40 | 43.9 | 63.2 | 80.5 |
| 2 | 7.7 | 13.2 | 23.60 | 45.0 | 63.9 | 78.2 |
| 3 | 7.3 | 13.8 | 28.3 | 57.8 | 78.0 | 91.6 |
| 4 | 6.6 | 12.2 | 25.1 | 49.0 | 70.7 | 87.0 |
| 5 | 7.3 | 13.4 | 25.5 | 48.8 | 68.2 | 85.2 |
| 6 | 7.3 | 12.9 | 24.3 | 53.0 | 71.7 | 85.4 |
| Avg. | 7.1 | 12.9 | 25.0 | 49.6 | 69.3 | 84.7 |
| % RSD | 6.2 | 5.0 | 7.1 | 10.4 | 7.9 | 5.6 |

STATISTICAL ANALYSIS FOR FIT TO ZERO ORDER RELEASE $T_{50\%} = 131.9$ minutes Dissolution Rate: 0.88 mg/minute (0.35%/min. 100 rpm paddle)

Correlation Coefficient (R) = 0.998 (excellent linearity) This example demonstrates that ingredient (d) is not absolutely necessary for achievement of zero order release by controlled surface erosion. It is, however, necessary for stability requirements.

EXAMPLE 5

1000 tablets of the following composition were prepared using the procedures of Example 1.

| Ingredient | Function Class | Per Tablet (mg) | % w/w |
|---|---|---|---|
| 5-Aminosalicylic Acid | a | 250 | 73.3 |
| Sodium chloride | b | 40 | 11.7 |
| Plasdone | f | 15 | 4.4 |
| Lactose Powder (200 mesh) | c | 30 | 8.8 |
| Stear-o-wet C | e/g | 6 | 1.76 |
| Sodium starch glycolate | d | 1.0 | 0.29 |
| Alcohol SDA-3A as a granulating solvent | | | |
| Total weight = | | 342 | |

FINISHED GRANULATION

Flow: Very good
Compressibility: Very good
Tablets: Compressed on rotary tablet press using ⅜" standard concave tooling, both upper and lower plain.
Hardness: 10 KP
Thickness: 0.176"
Friability: 0.08%
Average Tablet Weight: 344 mg.
Dissolution Data:
Dissolution Test Procedure: Same as in Example 2.

| Tablet Number | Cumulative % Dissolved of Label Claim Time, Minutes | | | | |
|---|---|---|---|---|---|
| | 15 | 30 | 60 | 120 | 180 |
| 1 | 8.7 | 14.8 | 40.5 | 65.4 | 86.0 |
| 2 | 14.6 | 29.6 | 48.1 | 73.1 | 95.0 |
| 3 | 8.8 | 17.7 | 35.7 | 64.4 | 90.0 |
| 4 | 9.6 | 19.0 | 38.0 | 67.8 | 94.0 |
| 5 | 10.1 | 21.0 | 45.9 | 74.9 | 98.0 |
| 6 | 9.7 | 20.0 | 48.1 | 77.1 | 98.9 |
| Avg. | 10.3 | 20.4 | 42.7 | 70.5 | 93.7 |
| % RSD | 21.4 | 24.6 | 12.6 | 7.5 | 5.2 |

STATISTICAL ANALYSIS FOR FIT TO ZERO ORDER RELEASE $T_{50\%} = 85.9$ minutes

Dissolution Rate = 1.257 mg/minute (0.5%/min. 100 RPM paddle)

Correlation Coefficient (R) = 0.995 (excellent linearity)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A solid, orally administrable pharmaceutical tablet composition having an enteric coating on its surface from which the active ingredient has a slow, zero order release rate attained without layers, beads or enteric materials and without relatively insoluble polymers, waxes or gums when administered orally, said tablet being compressed to a hardness of about 5–20 kg, and being either shaped as a sphere, or else having a ratio of tablet thickness to tablet diameter effective to permit tablet erosion and penetration control sufficient for controlled surface erosion thereof, comprising an essentially homogeneous, granulated mixture of:
   (a) an effective amount in the range of about 10–90 wt. % of 5-aminosalicylic acid as a pharmacologically active compound having a water solubility (20° C.) of less than 1/500 to 1/1000 (w/w);
   (b) about 1–40 wt. % of a surface controlling compound which is pharmaceutically acceptable in oral compositions and has a water solubility (20° C.) of about 1/1–1/40 (w/w);
   (c) about 2–20 wt. % of an erosion controlling compound which is pharmaceutically acceptable in oral compositions and has a water solubility of about 1/1–1/10 (w/w);
   (d) an amount in the range of about 0.05–1.0 wt. %, of a surface activator which is a disintegrating agent for pharmaceutical compositions at which amount the compound is ineffective as a disintegrating agent;
   (e) about 0.1–2.0 wt. % of a surfactant which is pharmaceutically acceptable in oral compositions, and, as necessary for tablet manufacturing purposes;
   (f) about 1–20 wt. % of a binder which is pharmaceutically acceptable in oral compositions; or
   (g) about 0.5–5.0 wt. % of a die wall lubricant which is pharmaceutically acceptable in oral compositions;
   the pharmacologically active ingredient thus having a slow, zero order release rate when administered orally, and the pharmacologically active compound not being a lithium compound, and not being penny shaped or pancake shaped wherein the ratio of thickness to diameter is too small for erosion and penetration control.

2. A pharmaceutical composition of claim 1 consisting essentially of all of ingredients (a)–(g).

3. A pharmaceutical composition of claim 1 wherein the amounts of ingredients are as follows:
 (a) 50–90 wt. %,
 (b) 3–30 wt. %,
 (c) 3–10 wt. %,
 (d) 0.05–0.5 wt. %,
 (e) 0.15–1.0 wt. %,
 (f) 1–5 wt. %, and
 (g) 1–4 wt. %.

4. A pharmaceutical composition of claim 1 having a spherical shape or a ratio of tablet thickness to tablet diameter of about 0.5±15%.

5. A pharmaceutical composition of claim 1 wherein all ingredients have a particle size distribution in the fine (U.S.P.) or very fine (U.S.P.) range.

6. A pharmaceutical composition of claim 1 further comprising, in place of a corresponding amount of active ingredient (a), 1–80 wt. % of an inert bulking excipient (h), pharmaceutically acceptable in oral compositions and having a water solubility (20° C.) of less than 1/500 to 1/1000 (w/w).

7. A pharmaceutical composition of claim 1 wherein (b) is a chloride, sulfate or phosphate of potassium, sodium or magnesium; calcium citrate, phosphate, lactate, gluconate or succinate; a mono- or di-saccharide or a correspondig polyhydric alcohol; a natural amino acid; or an organic carboxylic or sulfonic acid; and (c) is a mono- or di-saccharide or a corresponding polyhydric alcohol; a natural amino acid; or an organic carboxylic or sulfonic acid.

8. A pharmaceutical composition of claim 7 wherein (b) is an inorganic salt and (c) is a mono- or di-saccharide or a corresponding polyhydric alcohol.

9. A pharmaceutical composition of claim 8 wherein (b) is sodium chloride or calcium phosphate monobasic; and (c) is mannitol, lactose or sorbitol.

10. A pharmaceutical composition of claim 9 wherein
 (b) is sodium chloride or calcium phosphate monobasic;
 (c) is mannitol, lactose or sorbitol;
 (d) is sodium starch glycolate;
 (e) is sodium lauryl sulfate;
 (f) is polyvinylpyrrolidone; and
 (g) is calcium stearate.

11. A pharmaceutical composition of claim 5 prepared by first wet granulating ingredients (a), (b) and (f) if present, to form a homogeneous granulate; drying the resultant granulate; dry blending the remaining ingredients with the dried granulate and compressing the blend obtained into tablets of a hardness of 5–20 kg.

12. A method of orally administering an active ingredient (a) as defined in claim 1 to a patient in need of treatment with (a), such that (a) is released in vivo with a slow, zero order release rate, comprising orally administering to such a patient a pharmaceutical composition of claim 1.

* * * * *